United States Patent [19]

Reinhard

[11] 4,382,920

[45] May 10, 1983

[54] HORMONE-LIKE PEPTIDES AND USE THEREOF

[75] Inventor: Friedrich G. Reinhard, Dorfen, Fed. Rep. of Germany

[73] Assignee: Perignon Investments Ltd., Grand Cayman, Cayman Islands

[21] Appl. No.: 136,670

[22] Filed: Apr. 2, 1980

Related U.S. Application Data

[63] Continuation-in-part of Ser. No. 82,738, Oct. 9, 1979, which is a continuation-in-part of Ser. No. 50,408, Jun. 20, 1979, abandoned, which is a continuation of Ser. No. 916,874, Jun. 19, 1978, abandoned.

[51] Int. Cl.³ .................... A61K 37/00; C07C 103/52
[52] U.S. Cl. .............................. 424/177; 260/112.5 R
[58] Field of Search .................. 424/177; 260/112.5 R

[56] References Cited

PUBLICATIONS

Swan–Nature, vol. 1199, No. 4893, (Aug. 10, 1963), pp. 611 & 612.
Swan–The American Naturalist, vol. 103, No. 931, May–Jun. 1969, pp. 247–257.
Hollenberg et al.–J. Biochem., vol. 104, (1967), pp. 122–127.

*Primary Examiner*—Sam Rosen
*Attorney, Agent, or Firm*—Sherman & Shalloway

[57] ABSTRACT

Novel hormone-like peptides having an anti-metabolic biological activity have been isolated from the brains of estivating lungfish *Protopterus annectens* (Owen) and have the following formula:

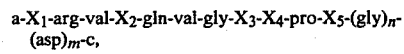

wherein, a, $X_1$, $X_2$, $X_3$, $X_4$, $X_5$, c, n and m are defined in the specification.

Both hypothermic and decreased oxygen consumption activity have been demonstrated in in vivo tests. In vitro tests have demonstrated suppression of DNA-production followed by a decrease in protein biosynthesis.

8 Claims, 10 Drawing Figures

Fig. 1

SEPHADEX G15 in 1M HaC

DOSE RESPONSE CURVE OF BRAIN EXTRACTS OF ESTIVATING (P) AND AROUSED LUNGFISH (S): EFFECT ON DNA-SYNTHESIS OF CHO-CELLS

Fig. 3

Fig. 4 — Effect of brain extracts of estivating (P) and aroused lungfish (S) on DNA and protein synthesis of CHO-cells: time response curve Fig. 5 — Effect of brain extracts of estivating (P) and aroused lungfish (S) on DNA-synthesis of liver cells of the rat

*Fig.6*

Biogel P2-400 in 0.04% TFA

*Fig.7*

DOWEX 50 WX4

Fig. 8

FIRST HIGH PRESSURE LIQUID CHROMATOGRAPHY ON REVERSED PHASE COLUMN

Fig. 9

SECOND HIGH PRESSURE LIQUID CHROMATOGRAPHY ON REVERSED PHASE COLUMN

Fig. 10

HORMONE-LIKE PEPTIDES AND USE THEREOF

RELATED APPLICATIONS

This application is a continuation-in-part of Ser. No. 082,738 filed Oct. 9, 1979, which in turn is a continuation-in-part of Ser. No. 050,408 filed June 20, 1979, now abandoned, which in turn is a continuation of Ser. No. 916,874 filed June 19, 1978, now abandoned.

BACKGROUND OF THE INVENTION

This invention is related to peptide substances extracted from the brains of estivating lungfish *Protopterus annectens* (Owen) and a process of producing same, and to a method of decreasing oxygen consumption and effecting hypothermia in animals. More particularly, this invention relates to novel hormone-like peptides and homologs and analogs thereof possessing an antimetabolic activity, and to the use of these peptides for their biological activity.

The lungfish, which estivates in the dry season, has the capacity to survive in a state of deep torpor for an uninterrupted period of more than two years.

Most of the previous investigations on lungfish have been conducted on the African lungfish *Protopterus aethiopicus* found in Lake Victoria, Africa. It has been found that the brain extracts from these estivating lungfish were capable of inducing torpor, metabolic supression, and hypothermia when injected intravenously into a test non-torpidator. The brains of estivating *Protopterus aethiopicus* were treated with acetic acid to form the biologically active extract. See Swan, et al., *Amer Naturalist*, 103(931): 247-257 (1969). However, it is noted that the lungfish used in this study were induced into estivation artificially. Furthermore, these lungfish belonged to a species different from that of the present invention.

It has been discovered by the present inventor that the brain extracts from estivating lungfish *Protopterus annectens* (Owen) found in Tchad, Africa, possess biological activity. This has been described in the inventor's prior applications mentioned above, especially Ser. No. 082,738.

The prior application discloses that a crude brain extract from estivating *Protopterus annectens* can be prepared by extracting with acetic acid and that the crude extract can be refined by subjecting the extract to successive gel and ion exchange chromatography steps.

Further work by the inventor has resulted in the isolation of a pure peptide having antimetabolic activity in animals and the ability to reversibly suppress synthesis of DNA and protein biosynthesis in in vitro tests. The additional purification was accomplished by successive high pressure liquid chromatography steps following the ion exchange chromatography.

SUMMARY OF THE INVENTION

Hormone-like peptides with biological activity having the following formula:

and wherein,
a is a member of the group consisting of a free amino group, and an acylated amino group;
$X_1$ is a member of the group consisting of ser, gln, glu, and pyr-glu;
$X_2$ is a member of the group consisting of lys and ser;
$X_3$ is a member of the group cinsisting of ser and asn;
$X_4$ is a member of the group consisting of ser, gln, and lys;
$X_5$ is a member of the group consisting of gln and ser;
c is a member of the group consisting of a free acid group and an acid amide group;
n=0 or 1 and
m=0 or 1, provided that when n=0, m=0,
pyr-glu being pyrrolidyl glutamic acid,
have been isolated from estivating lungfish *Protopterus annectens* (Owen). The peptides have been shown to possess antimetabolic activity, and especially the ability to reduce oxygen consumption and body temperature in animals, and the ability to reversibly suppress synthesis of DNA followed by the reversible suppression of protein biosynthesis in in vitro tests.

These peptides can therefore be used to lower oxygen consumption and to effect hypothermia by administering a pharmacolocically effective amount of the peptide to an animal. The biologically active peptide is prepared by a process comprising: (1) removing the brains of the lungfish which are estivating in their natural habitats; (2) extracting the brains with acetic acid and precipitating with ether to produce a crude powder product having biological activities; (3) subjecting the powder to gel and ion exchange chromatography steps to obtain a refined active product, and (4) subjecting the refined active product to two successive high pressure liquid chromatography steps to obtain a pure peptide having biological activity and a molecular weight in the range of about 1300 to 1580.

EXTRACTION AND PURIFICATION PROCEDURE

The brain extract of this invention is produced by a process comprising the following steps:

(1) Estivating lungfish *Protopterus annectens* (Owen) found in Tchad, Africa, are removed from mud beds during the dry season, which starts in December and continues through about the end of May. The beds are completely dry by about the middle and end of March. The fish are removed by digging around the fish so as to remove a cylinder of mud with the fish curled therewithin inside a paper-like cocoon. The head of the fish points upward and is connected to the surface through a breathing channel. It has been found that only the brain extracts from estivating lungfish possess the desired properties. Therefore, it is of utmost importance that the fish not be awakened or aroused during this removal. The cylinder of mud is split open and, immediately thereafter, the fish are decapitated. The skulls of the fish are drilled open so as to allow the removal of the entire brain and hypophysis which are then placed into acetone kept at a temperature of $-30°$ C. The entire process, beginning with splitting open the mud cylinder through the placing of the brains in the acetone, takes from about 60 to 90 seconds and should be completed within as short a period as possible. Contaminated acetone, i.e., acetone having brains placed therein, is replaced every half hour for a total of four times. Twenty to thirty brains are usually placed in 30 ml of acetone. The ratio weight of wet tissue (brains) to volume of acetone must be at least 1:5, and may be higher in order to absorb as much water as possible.

(2) The brains in acetone are then homogenized. This step may be performed with a Potter homogenizer for two minutes at 800 to 2,000 rpm in a 30 ml tube at $-10°$ C. As has been mentioned, the purpose of the homogenization is to extract water out of the brain, rather than destroying any cells.

(3) The homogenized mixture is transferred to a centrifuge tube and centrifuged. Centrifugation is continued for a period sufficient to produce a clear supernatant. This may be achieved by centrifuging for 50 minutes at 2,200 rpm at $4°$ C. The supernatant is discarded, with fresh acetone added to suspend the precipitate. The acetone is then removed by filtering through a Buchner funnel. The precipitate is dried at room temperature ($25°$ C.) under a nitrogen atmosphere. The precipitate dries to a powder and is stored at $-70°$ C.

(4) 1 M acetic acid is added to a known amount of the powder product. The mixture is homogenized for a period sufficient to destroy the cells. The homogenization may be conducted at 800 to 900 rpm for 5 minutes. The product is then transferred to a glass container since it has been found that polyethylene containers produce bad results.

(5) The solution, while being stirred, is heated in a boiling water jacket for a period sufficient to destroy proteins and enzymes in the extract. About 15 minutes are usually sufficient. Thereafter, the mixture is centrifuged to yield a clear supernatant. The centrifugation step should be carried out at as low a temperature as possible, preferably about $6°$ C., so as to prevent the destruction of peptides in the solution. The supernatant is separated from the precipitate. Another portion of 1 M acetic acid is then added to the precipitate, with the homogenization, heating and centrifugation steps being repeated. The solid brain extract is so treated for a total of four times, with the clear supernatant from each of the centrifugation steps being poured into a single container.

(6) To the supernatant liquid a small amount (about three drops) of octanol is added so as to prevent foaming.

(7) The solution is placed over a hot water bath to evaporate the acid. The flask is kept rotating and the open end of the flask is connected to a pump to remove the vapor. The evaporation is stopped when the liquid content of the flask has been reduced to a gel-like substance.

(8) Two equal portions of glacial acetic acid are used to dissolve the gel. The ratio of the total volume of acid used to weight of the starting material of step (4) is about 1 ml of acid to 100 mg of material. The gel is treated with the first portion of glacial acetic acid. The liquid portion is then transferred to a suitable container. The second portion of glacial acetic acid is then used to treat the gel and deposited into a container. The remainder of the gel is treated with a portion of acetone, with the acetone being deposited into the container thereafter. Upon the adding of acetone to the container, a magnetic stirrer is used to stir the solution. The stirring is needed to eliminate local high concentrations of acetone. Another portion of acetone is used to extract the gel, after which the mixture is also placed in the container. It is important that the volume ratio between the acetic acid and acetone used in this step is about 1:1 in order to dissolve all the desired material into the supernatant. The so-obtained mixture is centrifuged to obtain a supernatant and a precipitate. Suitable centrifuging conditions are: 5,200 rpm at $6°$ C. for 15 minutes.

(9) The supernatant from step (8) is decanted into a container. Ether in an amount of about 1.5 times the volume of the supernatant is added drop by drop to the supernatant to form a precipitate while the solution is being stirred vigorously. Other volume ratios have been found to be less desirable. The vigorous stirring is necessary so as to avoid high local concentrations of ether in the solution. After all of the ether has been added, the solution is stirred for an additional 15 minutes. Thereafter, the mixture is separated into a clean supernatant and a precipitate.

(10) The supernatant is discarded. The precipitate is dissolved in as small an amount of one normal acetic acid as possible. This usually takes from 10 to 15 ml. Large amounts of acetic acid should be avoided, since the solution is subsequently evaporated and the larger the amount, the longer the evaporation period.

(11) The solution is evaporated at about $50°$ C. Evaporation is stopped when the solution is reduced to a gel.

(12) The gel is dissolved in glacial acetic acid. The amount of glacial acetic acid used in this step is related to the amount of starting materials used. The ratio of glacial acetic acid to starting material of step (4) is about 1 ml of acid to 100 mg of material. Under vigorous stirring, ether is added to form a precipitate. The volume of ether used is about four times that of the volume of acetic acid used in this step in order to bring all of the desired product into the precipitate. It is important that the volume ratio of ether to acetic acid is about 4:1 since other ratios have found to be less desirable. After finishing adding the ether, the solution is stirred for an additional 15 minutes.

(13) The product of step (12) is then centrifuged to separate the precipitate.

(14) The supernatant of step (13) is discarded. In order to remove lipids, the precipitate is suspended in ether by means of stirring. After centrifuging, the supernatant is discarded and the precipitate again suspended in ether, stirred and centrifuged. This washing step by ether is repeated as many times as necessary, usually two to four times.

(15) After washing, the precipitate (crude extract) is sealed in a nitrogen atmosphere and permitted to dry. After drying, the precipitate is stored at −30° C.

(16) The brain extract from step (15) is refined or purified by gel chromatography. The extract is dissolved in 1 M acetic acid and fed to a column containing molecular sieve having a molecular weight fractionation range of about 1500. Molecular sieves with higher fractionation ranges have been found to be undesirable. The UV absorbance of the solution is monitored. The fractions which show biological activity are subjected to further refining in step (17).

As a preferred embodiment of this step, the brain extract-containing acetic acid is fed a column containing SEPHADEX G15 molecular sieve, a bead-formed dextran gel manufactured by Phasmacia Ltd., Uppsala, Sweden. The column is 3.1 cm in diameter and 130.2 cm in length. 1 M acetic acid is used as the eluant and an effluent velocity of 10.5 ml per 20 minutes per fraction maintained. It has been found that higher effluent velocities produce undesirable results. As to the eluants, the following have been determined to be undesirable: 1 M formic acid, 30% propionic acid, and 0.005 M ammonium bicarbonate. A response curve comprising three primary peaks is obtained. Fractions corresponding to peak numbers 2(G15 II) and 3(G15 III) are found to be biologically active.

(17) The active fraction (G15 II) of step 16 is further refined by a second gel chromatography step. A portion of the freeze dried material from the second pool (G15 II) of step (16) is dissolved in 0.04% trifluoroacetic acid and then fed to a gel chromatography column containing molecular sieve having a fractionation range of from about 1800 to about 300. The UV absorbance of the solution is monitored. The fractions which show biological activity are subjected to additional refining in step (20).

As a preferred embodiment of this step, the trifluoroacetic acid solution is fed to a molecular sieve column. The column is 1 cm in diameter and 136 cm long. BIO-GEL P2-400 is a suitable molecular sieve. The eluant is 0.04% trifluoroacetic acid and the effluent velocity is 2 ml per 40 minutes.

(18) Brain extracts obtained from the active fractions from step (17) are further refined by a cationic ion exchange resin chromatography step. The extract is dissolved in 2% acetic acid and fed to a column containing an equilibrated cationic ion exchange resin. After an initial elution step at the pH of the equilibrated column resin, a linear pH gradient is used for elution. The UV absorbance after ninhydrin reaction is monitored.

As a preferred embodiment of this step, the brain extract-containing acetic acid is fed to a cationic ion exchange resin column. The column is 1 cm diameter and 28 cm in length. DOWEX 50-W-4 is a suitable exhange resin. The resin has been equilibrated to pH 3.24 at 51° C. with 0.2 molar pyridine acetate solution. The initial elution step is with 100 ml of the 0.2 molar pyridine acetate at pH 3.24. Thereafter, a linear pH gradient is used for elution with the eluants being 3 M pyridine acetate at pH 5.15 and 0.2 M pyridine acetate at pH 3.24

(19) Brain extracts obtained from the active fraction from step (18) are further refined by two successive high pressure liquid chromatography steps, the programs used being taught by F. Lottspeich in *Journal of Chromatography* (in publication).

In the first high pressure liquid chromatography step, the active fractions from step (18) are vacuum dried and dissolved in 0.005 mM $Na_2HPO_4$ solution. The pH of the solution is adjusted to 3.1 with phosphoric acid. The solution is fed to a 5μ Merck RP 18 Hibar Reversed Phase column having a diameter of 4.6 mm and a length of 240 mm. The eluant is acetonitrile (Uvasol-Merck). A gradient of 5% to 45% in 30 minutes is used. The UV absorbance of the solution at 210 nm is monitored.

The active fractions obtained from the first high pressure liquid chromatography step are subjected to a second high pressure liquid chromatography step using a column having the same contents and dimensions of those in the first step. The active fractions are dissolved in 0.005 M $KH_2PO_4$ and adjusted to a pH of 3.1 with phosphoric acid. The eluant used is acetonitrile (Uvasol-Merck). A gradient of 5 to 25% in 30 minutes is used. The UV absorbance of the solution at 210 nm is again monitored. Active fractions of the eluted solution are collected to obtain peptides having high purity.

ANALYSIS OF PRODUCT

The biologically active peptide product obtained in step (19) is tested to determine: (1) their amino acid composition; (2) the sequence of the amino acids contained in the peptides; and (3) their biological activity.

The product is tested for its amino acid composition using techniques well known in the art. For the present product, it is found that it has the following composition:

| | |
|---|---|
| 0 or 1 | asp |
| 3 | ser |
| 2 | gln |
| 1 | pro |
| 1 or 2 | gly |
| 1 | val |
| 1 or 2 | lys |
| 1 | arg |

The abbreviations for the various amino acid residues are standard and, for convenience, are tabulated below:

| Abbreviation | Amino Acid |
|---|---|
| Ala | Alanine |
| Arg | Arginine |
| Asn | Asparagine |
| Asp | Aspartic acid |
| Cys | Cystine (half) |
| Glu | Glutamic acid |
| Gln | Glutamine |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |

The peptide of step (19) is also tested for the sequence of amino acids contained therein. By using test procedures well known in the art, the following sequence is obtained:

a-$X_1$-arg-val-$X_2$-gln-val-gly-$X_3$-$X_4$-pro-$X_5$-(gyl)$_n$-(asp)$_m$-c, wherein
a is a free amino group or an acylated amino group,
$X_1$ is ser, gln, glu or pyr-glu,
$X_2$ is lys or ser,
$X_3$ is ser or asn,
$X_4$ is ser, gln, or lys,
$X_5$ is gln or ser,
c is a free acid group or an acid amide group,
n=0 or 1, and
m=0 or 1, provided that when n=0, m=0,
pyr-glu being pyrrolidyl glutamic acid.

Acid groups in the side chains of the peptide may be free acid groups or acid amide groups, whereas, amino groups in the side chains may be free amino groups or acylated amino groups.

The peptide has a molecular weight of from 1350 to 1560.

The present peptide can be synthesized by one of ordinary skill in the art using methods which have now been well developed and are conventional.

The peptide of the present invention has been found to have utility because of its antimetabolic activity. Examples of antimetabolic activity include decreasing oxygen consumption in animals, inducing hypothermia in animals, and causing suppression in DNA production followed by a decrease in protein biosynthesis in animal cells. The above effects from the administration of the present peptide to animals have been found to be reversible, i.e., the effect decreases after reaching a peak, and after the lapse of sufficient time, the condition in the animal returns to normal, with the animal showing no after effects as a result of the administration of the peptide.

A pharmacologically effective dosage of the peptide to be administered to animals ranges from about 200 to about 400 µg/kg of body weight.

The peptide of the present invention contains amino acids which are in the L configuration since the peptide is extracted from a natural product. However, in synthesizing the present peptide, amino acids in either the L or D configuration can be used.

EXAMPLES

To better illustrate the present invention, the following examples are provided. However, it is emphasized that these examples are for illustrative purposes and should not be considered to be limiting.

Experimental equipment used in these examples include a Potter Homogenizer made by the Brown Co., a centrifuge made by the I.E.C. Co., and a UV absorption detection made by 15 CO.

The following examples are directed to the preparation of a crude brain extract.

EXAMPLE 1

1674 mg of the powder obtained in step (3) is placed in a 30 ml homogenizer tube and 16.8 ml of 1 N acetic acid is added. The mixture is homogenized for 5 minutes at 800–900 rpm. The homogenate is then transferred to a glass tube.

The mixture is heated, while being stirred, in a hot water jacket at 100° C. for 15 minutes. Thereafter, the mixture is placed in a 50 ml centrifuge tube and centrifuged at 5200 rpm at 6° C. until a clear supernatant is obtained. The supernatant is decanted into a 250 ml evaporator flask. The precipitate is suspended with 16.8 ml of 1 N acetic acid, with the homogenizing, heating and centrifuging being repeated. The brain extract is so treated for a total of four times, with the clear supernatant from each of the centrifugation steps being poured into the evaporator flask.

To the so-called supernatant (about 17 ml), 3 drops of octanol are added in order to prevent foaming. The solution is placed over a hot water bath at 50° C. to evaporate the acid and water. Evaporation is stopped when the volume has been reduced to about 3 ml whereupon a gel-like substance is obtained.

8.4 ml of glacial acetic acid is poured into the flask which is then swirled to dissolve the gel. The solution is transferred to a 50 ml centrifugal tube. The gel is further contacted with 8.4 ml of glacial acetic acid, the solution being added to the centrifuge tube. The flask is washed twice with two 8.4 ml portions of acetone, which are added to the centrifuge tube. Upon the addition of the acetone to the tube, the solution is stirred with a magnetic stirrer.

The contents of the centrifuge tube is centrifuged at 5200 rpm at 6° C. for 15 minutes. The clear supernatant is deposited into a 100 ml centrifuge tube as 50.4 ml of ether is added dropwise under vigorous stirring. The agitation is continued for 15 minutes after all of the ether has been added. The resultant mixture is centrifuged at the same conditions as mentioned above.

The supernatant shows no activity and is discarded. The precipitate is dissolved in about 10 ml of 1 N acetic acid and deposited in an evaporator flask. The solution is evaporated at 50° C. until the volume has been reduced to about 1 ml, where a gel-like substance is formed.

The gel is dissolved in 16.8 ml of glacial acetic acid and transferred to a 100 ml centrifuge tube as 67.2 ml of ether is added under strong agitation. The agitation is continued for 15 minutes after all of the ether has been added. The mixture is then centrifuged.

The precipitate is washed by suspending in 70 ml of ether and centrifuging, with the supernatant being discarded. The washing is repeated for a total of 4 times. The precipitate is then sealed in a nitrogen atmosphere and dried. A yield of 748 mg is obtained.

EXAMPLES 2–13

The procedure outlined in Example 1 is repeated, using different amount of starting material. The results are summarized in Table 1.

TABLE 1

| Example No. | Amount of Starting Material, mg. | Amount of Crude Extract, mg. | |
| --- | --- | --- | --- |
| 2 | 3200 | 1776 | 55.5 |
| 3 | 1270 | 604 | 47.5 |
| 4 | 670 | 313 | 46.7 |
| 5 | 1600 | 646 | 40.4 |
| 6 | 3020 | 1026 | 34.0 |
| 7 | 1600 | 1020 | 63.8 |
| 8 | 1600 | 848 | 53 |
| 9 | 1600 | 715 | 44.7 |
| 10 | 3200 | 1661 | 51.9 |
| 11 | 1270 | 604 | 47.6 |
| 12 | 3200 | 1305 | 40.1 |
| 13 | 1205 | 729 | 60.5 |
| | | | 48.8 |

EXAMPLE 14

Figure 1:
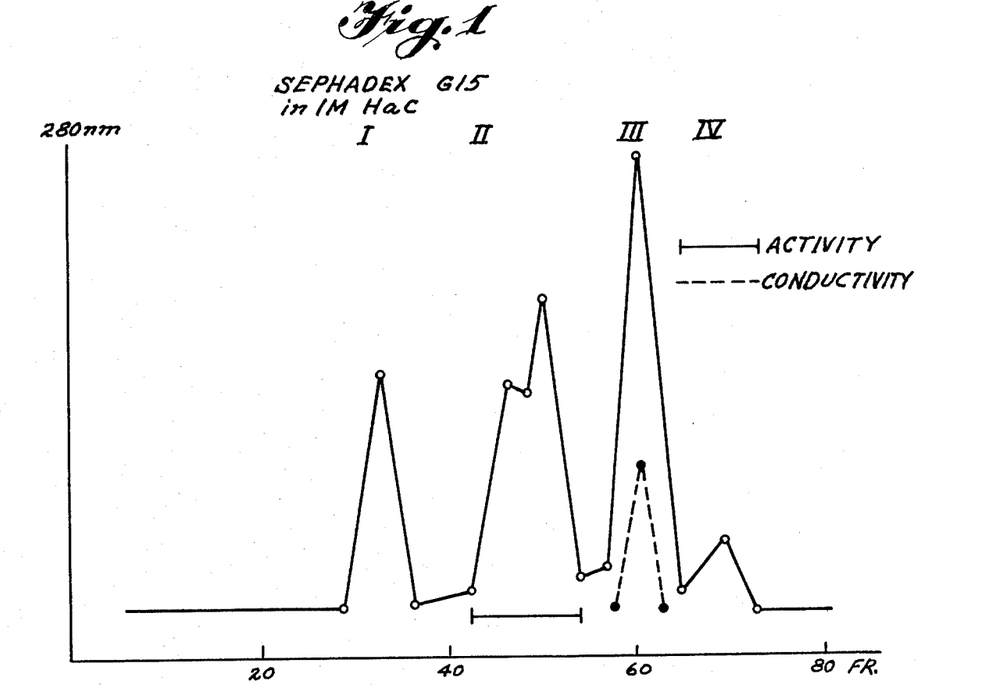
FIG. 1 shows the absorbance at 280 nm vs. fraction number plot for fractions obtained in Example 14.

748 mg of the product obtained in Example 1 is dissolved in 10 ml 1 N acetic acid. The solution is fed to a gel chromatography column containing SEPHADEX G15 molecular sieve. The column's dimensions are 3.1 cm diameter and 130.2 cm length. The flow rate of the effluent is 10.5 ml/20 min/fraction. 1 M acetic acid is used as the eluant. In FIG. 1, the UV absorbance at 280 nm vs. fraction number is shown. As will be noted in FIG. 1, there were at least three peaks in the UV absorbance; A first pool of material constituting fractions 27 to 34 was made (G15 I). A second pool of material constituting fractions 35 to 45 was made. Hereinafter, this will be referred to as G15 II. A third pool of material constituting fractions 46 to 60 was made (G15 III). Freeze drying of the G15 II pool gave 21 mg of product. Freeze drying of the G15 III pool gave 425 mg of product.

Also, plotted is DNA activity (as discussed hereinafter) vs. fraction number, as well as electrical conductivity vs. fraction number. It is to be noted that in this particular run with SEPHADEX G15, fractions numbered 42 to 54 showed DNA activity and were non-conductive. Fractions number 57 to 62 were electrically conductive. Electrical conductivity of these solutions is related to the presence or absence of various salts, such as sodium chloride, potassium chloride, and calcium acetate, in the solution. Accordingly, these fractions may be further characterized into two main groups: those having antimetabolic activity and being non-electrically conducting (salt free) and the other group, electrically conducting (salt containing) and having hypothermic activity, but not tested for its antimetabolic activity.

COMPARATIVE EXAMPLES 1-4

To show the significance of acetic acid in the extraction step (steps (4)–(15) in the instant specification), the following experiments, wherein the 1 M acetic acid and glacial acetic acid are replaced by those listed below, are conducted.

Comparative Example 1 acetone
Comparative Example 2 98% acetic acid
Comparative Example 3 ethanol/hydrochloric acid 3:1
Comparative Example 4 water The products obtained in these experiments show no effects when injected into laboratory test animals.

COMPARATIVE EXAMPLES 5-8

The following experiment is conducted to show the significance in the selection of the eluant in the gel chromatography refining steps.

1600 mg of product from step (3) in the specification is dissolved in 1 M acetic acid. The procedures outlined in Example 14 is repeated, except that trifluoroacetic acid is used as the eluant in the chromatography step. The UV absorbance of the final product fractions shows seven peaks, none of which is well developed. Furthermore, activity is spread out among the fractions, showing that the crude extract has not been refined or concentrated.

In addition, the following runs are made, using one of the materials shown in Table 2 as the eluant in the gel chromatography step.

TABLE 2

Comparative Example 6 1 M formic acid
Comparative Example 7 30% propionic acid
Comparative Example 8 0.005 M ammonium bicarbonate The products obtained in these examples do not yield fractions with high activity. Instead, low activity is found in a large number of fractions, indicating that the extract has not been refined.

COMPARATIVE EXAMPLES 9-10

These examples illustrate the importance of the effluent flow rate in the gel chromatography steps. Example 14 is repeated except the effluent flow rate is set at 30 ml/20 min/fraction and 60 ml/20 min/fraction, in Comparative Examples 9 and 10, respectively. Once again, low activity is found in a large number of fractions, indicating that little refining has been achieved.

COMPARATIVE EXAMPLE 11

In this example, different volume ratios of acetone used in step (8) in the specification are tested. The ratios tested are: 0.5, 1.5 and 2.0 volume acetone to 1 volume of acetic acid. It is found that these ratios yield a substantial smaller amount of product.

COMPARATIVE EXAMPLE 12

The significance of the 1.5:1 volume ratio of ether to the supernatant in step (9) is shown in this example. A series of runs are made using ratios of 0.5, 1.0 and 2.0. The results show that a substantially smaller amount of product is obtained.

COMPARATIVE EXAMPLE 13

To determine the importance of the 4:1 volume ratios of ether to acetic acid in step (12), comparative tests are conducted. The volume ratios tested include 3, 5, 6, 7 and 8. The results show that a substantially smaller yield of product is obtained.

EXAMPLE 15

To show that the pool G15 II of the brain extract obtained in Example 14 possesses biological activity, the following tests are conducted on mice and rats.
  Specification on mice:
    Type: Out-breed, white NMRI
    Sex: Male
    Average body weight: 24–27 gm
    Diet: Standard food pellet
  Test conditions:
    Mice fasted 12–15 hrs. prior to testing (water given during this period)
    Mice all separated from one another
    Mice kept in quiet and dark environment
    Room temperature maintained at 22.5° C. during fasting & testing
    Testing time: 1 p.m.–3 p.m. each day
  Test solution is prepared by:
    (a) dissolving a known amount of the refined brain extract in 0.4 ml of 0.1 M sodium acetate buffer, with the pH of the solution being adjusted to from about 7.0 to about 7.4 (the physiological pH of mouse being about 7.35); or
    (b) dissolving a known amount of the refined brain extract in 0.4 ml of trishydrochloric buffer and adjusting the pH of the solution to from about 7.0 to about 7.4 by titrating with microdrops of 1 M or 0.1 M sodium hydroxide solution.

Volume of solution injected into mice: from 0.1 ml to 0.5 ml.

Solution is at room temperature when injected into mice.

Test procedure:
Mouse is placed in restrainer
Injection is made in the tail vein
Injection time: 2 minutes
Body temperature is measured by inserting a thermistor into the anal cavity to a depth of 1½ cm (thermistor is made by Thermovit, Fu. Armatherm, Lemgo, W. Germany)
Temperature measurements are begun immediately after injection, i.e., 2 minutes after injection started Tests have also been conducted on rats having the following specifications:
Type: white, WISTAR
Sex: male
Average body weight: 250–300 gm
Diet: standard food pellet
Test Conditions: (same as above)
Test procedure:
Rat is anesthetized with ether for three minutes (ether has no effect on body temperature)
Skin is cut open to expose leg vein
Injection time: 2 minutes
Ether is removed and opening stitched closed
Body temperature is monitored immediately after administration of ether The following visual observations of the mice after injection are made:

(1) no shivering developed;

(2) mice become lethargic, move slowly; and do not respond to touch or tapping on box in which they are kept;

(3) mice appear to be weak;

(4) mice refuse food;

(5) mice keep their eyes closed and stay in the same spot;

(6) mice regain normal behavior slowly as effects of extract wears off;

(7) no observable after-effects.

The above observations also apply to rats injected with the brain extract.

Figure 2:
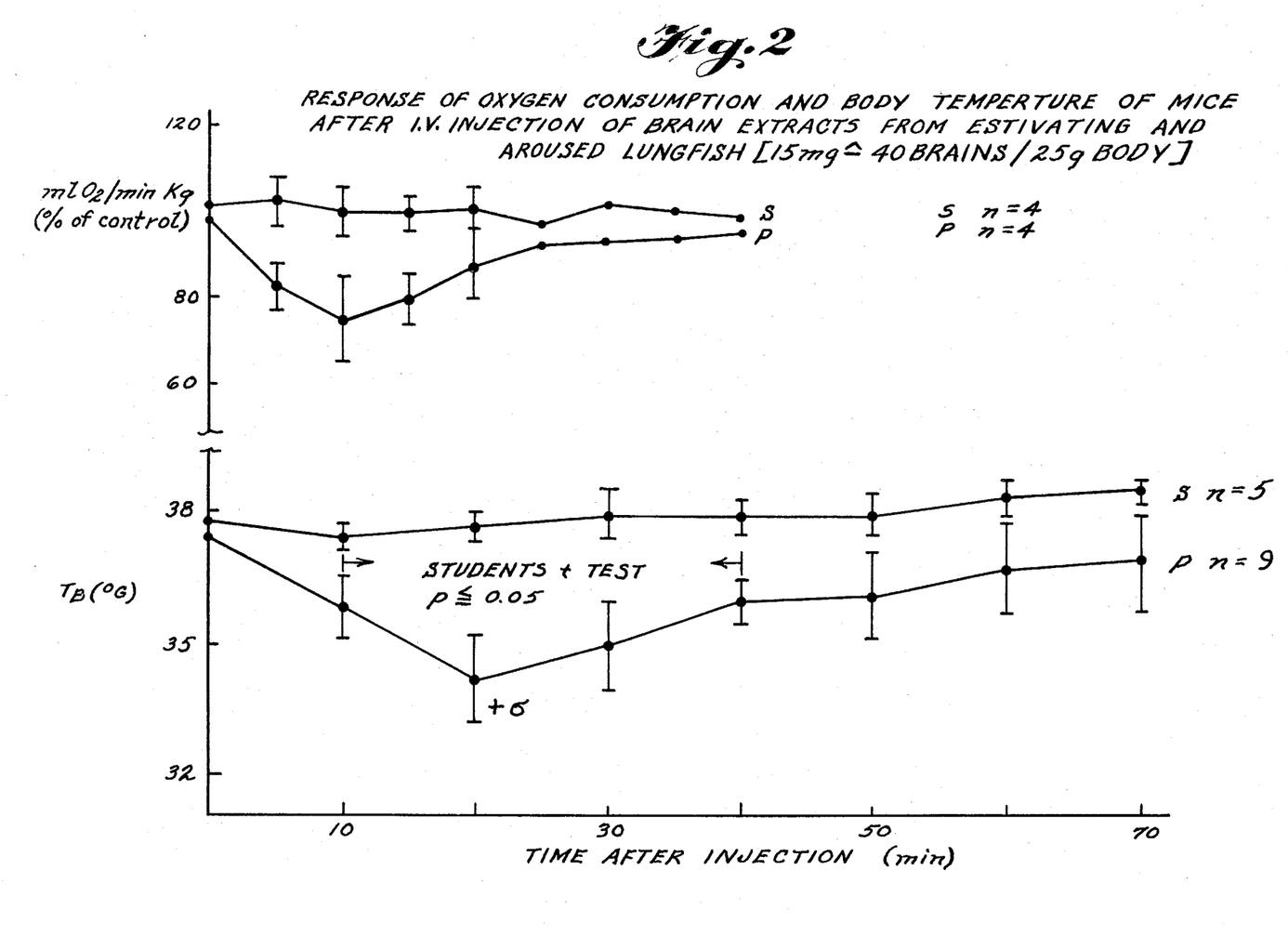
FIG. 2 shows the results of Examples 16 & 17 for response of oxygen consumption and body temperature of mice after I.V. injection of material of G15 II from estivating and aroused lungfish.

The results of the experiments on the lowering of body temperature are shown in FIG. 2.

In this series of experiments, the lowering of the body temperature of mice after intravenous injection of the second pool in Example 14 is determined. As a comparison, a similar extract from an aroused lungfish which has been purified in accordance with procedures in Examples 1–14 is used in the same manner. The extract obtained from the brain of 40 lungfish is used. Five mice are used in obtaining the data on the aroused lungfish and nine mice are used for the data on the estivating lungfish.

A review of these results shows that the body temperature of the mice falls in a period of about 20 minutes to its maximum effect of 3° to 4° C. Thereafter, the temperature starts to rise with the whole effect lasting about 30 to 40 minutes. As a comparison, the extract from the aroused lungfish shows essentially no lowering of body temperature.

The visual observation of the mice during the experiments is consistent with the results of the experiments as given above.

EXAMPLE 16

In addition to having the biological activity of hypothermia in animals, the following tests demonstrate that the second pool (G15 II) of material from the separation with SEPHADEX G15 molecular sieve, i.e., Example 14 is also effective in lowering the oxygen consumption of mice. The results obtained are also given in FIG. 2.

In this series of experiments, the decrease in the oxygen consumption of mice after intravenous injection of the second fraction of brain extract in Example 14 is determined by using a Beckman F3 analyzer. As a comparison, a similar extract from an aroused lungfish is purified in accordance with the procedure of Example 1–14. Again, the extracts obtained from brains of 40 lungfish are used. Four mice are used in obtaining the data on the aroused lungfish and four mice are used for the data on the estivating lungfish.

A review of these results show a significant decrease in the oxygen consumption after about 5 minutes with the maximum decrease occuring after about 10 minutes. Thereafter, the oxygen consumption starts to rise with the whole effect lasting about 30 to 40 minutes. It is to be noted that the maximum effect is the lowering of oxygen consumption to about 65% of the control. As a comparison, the similar extract from the aroused lungfish shows essentially no change in the oxygen consumption.

A comparison of the data on oxygen consumption and body temperature changes shows that the first effect (timewise) after the injection of the subject extract is a decrease of the oxygen consumption followed by a lowering of the body temperature. This data leads to the conclusion that this extract has antimetabolic effect, i.e., its first mode of action is to decrease the oxygen consumption, with the secondary effect being to decrease the body temperature.

The visual observations of the mice are the same on the series of the experiments as given above.

A similar set of experiments, i.e., measuring changes in body temperature of mice and changes in oxygen consumption are run using (1) an extract from cow brain without the cortex and (2) an extract from rat brain without the cortex, and (3) an extract from trout brain (whole brain). No effects are noted in body temperature and oxygen consumption.

In this work, oxygen consumption is measured against a control of the mean of five observations of mice under standard room temperature and pressure prior to the injection. Consumption of oxygen was measured as ml/min. × kilograms of body weight of mouse and expressed as percent of control.

COMPARATIVE EXAMPLE 14

For comparative purposes, control experiments are conducted to show that only brain extracts from estivating lungfish have hypothermia effect. These experiments are summarized in Table 3. It is noted that the brain extracts of non-estivating lungfish have no effect on the body temperature of the test animals.

TABLE 3

| SUBSTANCE | ml. inj. | Test Animal | n | 0 | 2 | 5 | 10 | 20 | 30 | 40 | 50 | 60 min. |
|---|---|---|---|---|---|---|---|---|---|---|---|---|
| EXTRACT OF NON-ESTIVATING LUNGFISH BRAIN | Equiv. 12 brains | rats | 20 | 37.0 | 37.5 | 37.9 | 37.2 | 37.0 | 37.1 | 36.9 | 36.5 | 36.9 |
| EXTRACT OF BEEF BRAIN | Equiv. 1/2000 brains | mice | 7 | 36.9 | 36.6 | 37.1 | 37.5 | 37.2 | 37.3 | 37.0 | 36.9 | 37.0 |
| 0.1 M SODIUM ACETATE | 0.5–1.0 | mice | 7 | 37.2 | 38.0 | 38.6 | 38.9 | 38.7 | 38.8 | 38.8 | 38.6 | 38.1 |
| 1.0 M SODIUM ACETATE | 0.4–0.9 | mice | 5 | 37.0 | 36.5 | 37.5 | 38.0 | 38.3 | 38.5 | 38.0 | 38.1 | 38.2 |
| 3.0 M SODIUM ACETATE | 0.2–0.3 | mice | 5 | 37.5 | 36.0 | 36.2 | 37.0 | 38.0 | 37.7 | 38.1 | 38.6 | 38.5 |
| 3.0 M NaCl | 0.2 | mice | 3 | 36.0 | 34.9 | 36.5 | 38.1 | 37.9 | 37.4 | 37.4 | 37.6 | 37.7 |
| 3.0 M KHCO$_3$ | 0.03 | mice | 2 | 37.1 | 34.7 | 35.0 | 36.5 | 37.8 | 37.9 | 38.4 | 38.4 | 38.0 |
| 1.0 M KHCO$_3$ | 0.05 | mice | 2 | 38.0 | 37.2 | 37.3 | 38.5 | 39.5 | 39.0 | 39.1 | | |
| 0.3 M KHCO$_3$ | 0.16 | mice | 5 | 37.6 | 36.3 | 37.2 | 38.0 | | 38.3 | | 38.3 | |
| TRYPTOPHAN | 1.5 mg | mice | 7 | 36.9 | 36.4 | 36.8 | 37.1 | 37.4 | 36.5 | 36.8 | 37.0 | 36.9 |
| GLUTARIC ACID | 1.5 mg | mice | 6 | 36.6 | 36.5 | 37.0 | 38.1 | 38.5 | 38.5 | 38.4 | 38.6 | 39.0 |
| ASPARTIC ACID | 2 mg | mice | 6 | 36.7 | 35.5 | 36.7 | 38.0 | 37.5 | 37.6 | 37.8 | 37.8 | 37.8 |
| 0.1 M Tris HCl BUFFER | 0.5 | mice | 7 | 36.7 | 35.0 | 36.7 | 37.8 | 39.0 | 39.6 | 39.2 | 39.6 | 38.2 |

Extracts of non-estivating lungfish and beef brain produced by identical procedures as for active extracts (steps (1–15))
n = number of animals
min - minutes
all solutions titrated to pH 7.0–7.4 by NaOH

EXAMPLE 17

The following experiment is conducted to determine whether the refined brain extract from the second pool from Example 14, is subjected to attack by enzymes. The extract is incubated with the materials shown in Table 4 under the listed conditions.

It is found that the hypothermia and oxygen consumption reduction effects in mice of the active materials can be destroyed by pronase P. This is shown in Table 4.

TABLE 4

| | | SECOND POOL (G15 II) | | | |
|---|---|---|---|---|---|
| Set | Material | Microgram enzyme Microgram material | Time of incubation hours | Temp. of incubation, C.° | pH | Effect |
| 1. | Pronase P$^a$ | 2.4 × 10$^{-4}$ | 1.0 | 39 | 7.10 | 0 |
| 2. | Pronase P$^a$ | " | " | " | 7.10 | 0 |

These tests show that the active materials of the invention are destroyed by pronase enzyme. Since pronase enzyme are only known to destroy peptides these tests confirm the inventor's hypothesis that the active materials are peptides.

EXAMPLE 18

A series of tests is conducted to determine the difference in effective dosages in the products obtained at the end of various steps in this invention, e.g. steps (3), (15), (16), (17) and (18) of the instant process. The test results are summarized in Table 5.

According to Table 5, the specific activities of the brain extracts are increased substantially as a result of the purification steps.

TABLE 5

| | PREPARATIVE RUN (1745 Brains) | | | | |
|---|---|---|---|---|---|
| PURIFICATION RUN | BRAINS | μ of Brain Extract μ/Brain | | Enrichment (– fold) | Purification Factor | ng/Dose* |
| Acetone powder | 1745 | 62,000,000 | 35,530 | | | |
| Ether powder | | 3,000,000 | 17,765 | 2 | 2.0 | |
| 1st run on Sephadex G15 | | 1,460,000 | | 42.4 | 21.2 | |
| 2nd run on Sephadex G15 | | 960,000 | | 64.6 | 1.5 | 275,000 |
| Run on Biogel P2 | | 330,000 | | 190 | 3.2 | 85,000 |
| Run on Dowex 50 | 120 | 1,500 | | 2,890 | 13.6 | 6,250 |
| 1st run on HPLC Reversed Phase | 50 | 6 | | 300,000 | 104 | 60 |
| 2nd run on HPLC Reversed Phase | 50 | 3 | | 590,000 | 2 | 30 |

*to depress DNA synthesis by at least 25% (CHO cells) 1 dose 0.5 brain.

EXAMPLE 19

In order to further test the metabolic effects of the brain extract obtained as the second pool (G15 II) in Example 14, its effect of DNA-synthesis on Chinese hamster ovary cells (CHO) is measured. The seed stock of CHO was obtained from the American Type Culture Collection, Rockville, Md. (ATTC CHO-KI).

In general the test procedure with the CHO is as follows:

1. Seed stock obtained from ATCC is placed in liquid nitrogen.

2. As needed new seed is removed from liquid nitrogen, supplied with new Ham's F-12 media which contained 10% Fetal Calf Serum.

3. Plastic plates containing 2–4×10$^5$ cells/ml are pre-incubated for 4 hours at 37° C. in an atmosphere containing 0.1% CO$_2$.

4. After pre-incubation, sample of various concentrations of test material are added to the plates. For control purposes, plates containing only Ham's F-12 are used. These plates are then incubated for the desired period of time.

5. After the incubation period, cells are washed 5 times with 2 mM cold Thymidine and then the cells are killed with 7% trichloracetic acid solution.

6. The dead cells are scraped from the bottom of the plates and filtered through a GFC filter. The thymidine incorporation is measured by liquid scintillation counting.

7. The incorporated thymidine is measured in decompositions per minute and expressed as percent of control.

8. Each test is done with three or more plates of material and then each test is repeated at least three times.

Figure 3:
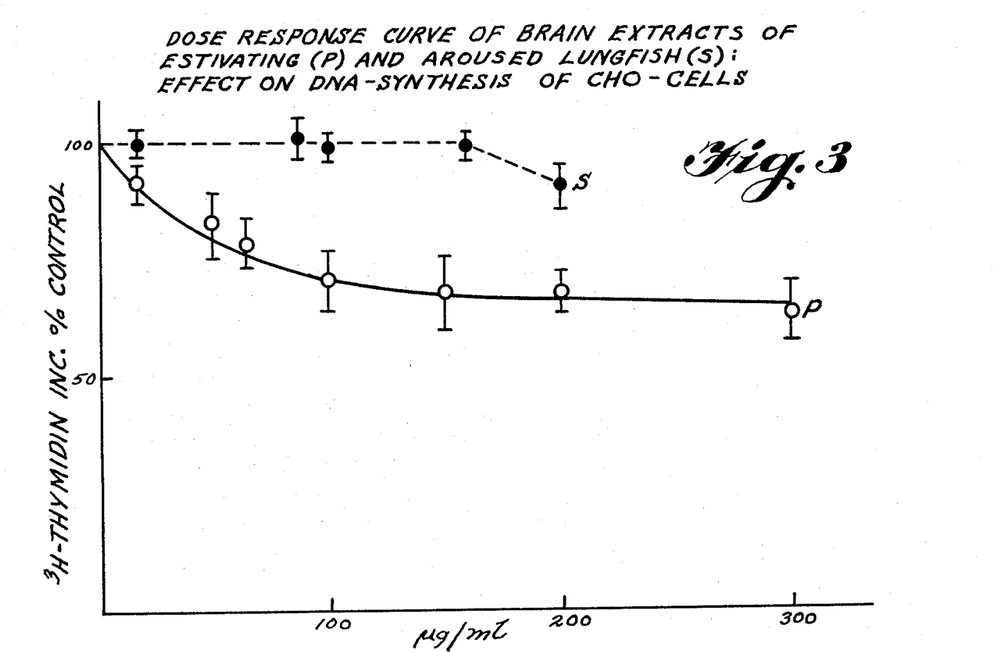
FIG. 3 shows the dose-response curve of material of G15 II of estivating and aroused lungfish: Effect on DNA-synthesis of CHO-cells.

The result of this testing is shown in FIG. 3 wherein a dose-response curve of the extracts of estivating and aroused lungfish has been plotted. The test conditions are label time, 40 minutes; incubation time, 60 minutes.

It is to be noted that this dose-response curve shows a maximum of about 35% decrease in DNA synthesis which is approached asymptotically at a concentration of G15 II of 100 µg/ml.

Figure 4:
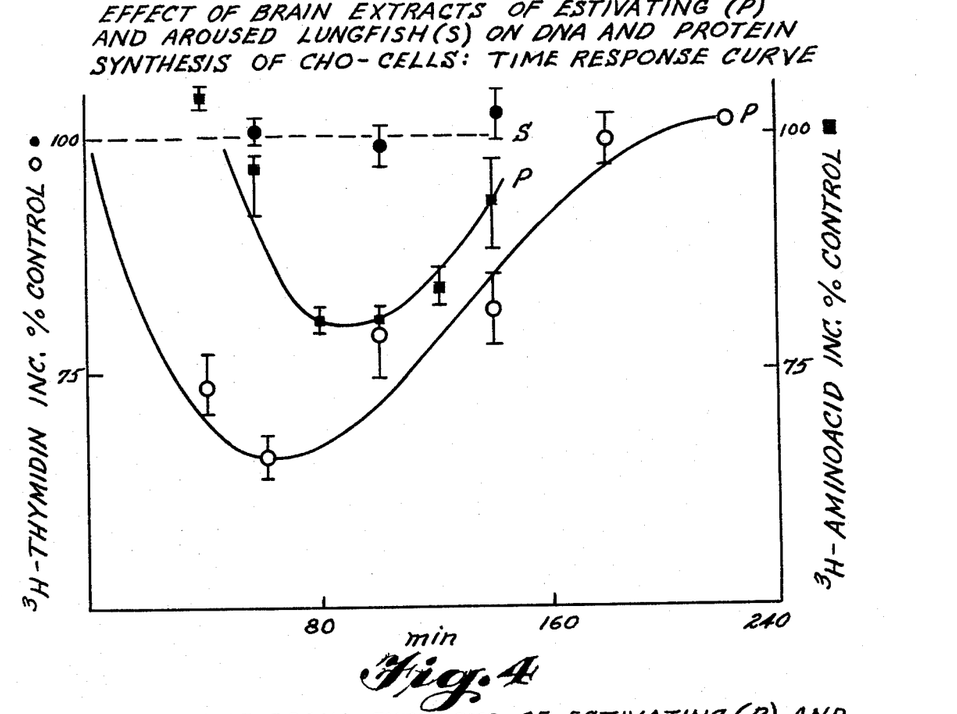
FIG. 4 shows the effect of material G15 II of estivating and aroused lungfish on DNA-synthesis and protein synthesis of CHO cells; time-response curve.

The effect of these brain extracts of the estivating and aroused lungfish on DNA synthesis of CHO cells is further shown in FIG. 4, where data are presented in the form of a time-response curve. This, again, is a measure of the inclusion of $^3$H-Thymidine into the DNA of CHO cells. The results are expressed on the basis of percentage differences for the two extracts as measured against a control.

Further observations, during the experiments, of the CHO cells indicated the effects noted are not due to a toxic effect of the test materials on the cells. Thus, the viability of the cells is always good as shown by the exclusion of the Trypan blue in a dye exclusion test. Likewise, it is noted that the cells stick to the plastic disk, i.e. cells living, and not float to the top.

EXAMPLE 20

In order to further test the metabolic effects of the brain extract obtained as the second pool (G15 II) in Example 14, its effect on protein synthesis of Chinese hamster ovary cells (CHO) is measured. The seed stock of CHO is obtained from the American Type Culture Collection, Rockville, Md. (ATTC CHO-KI).

In general, the test procedure with the CHO is as follows:

1. Seed stock obtained from ATTC is placed in liquid nitrogen.

2. As needed, new seed is removed from liquid nitrogen, supplied with new Ham's F-12 media, which contains 10% fetal calf serum.

3. Plastic plates containing 2-4×10$^5$ cells/ml are pre-incubated for 6 hours at 37° C. in an atmosphere containing 0.1% CO$_2$.

4. The media are changed to Ham's F-12 without fetal calf serum.

5. After pre-incubation, a sample of various concentrations of test material is added to the plates. For control purposes, plates containing only Ham's F-12 are used. These plates are then incubated for the desired period of time.

6. After the incubation period, the protein is precipitated with 10% trichloroacetic acid and the precipitate dissolved in 0.1 N NaOH.

7. Protein synthesis is measured by incorporation of a labelled cocktail of amino acids.

8. The incorporated $^3$H-amino acids are measured in decompositions per minute and expressed as percent of control.

9. Each test is done with three or more plates of material and then each test is repeated at least three times.

The effect of these brain extracts of the estivating and aroused lungfish on protein synthesis of CHO cells is shown in FIG. 4, where data are presented in the form of a time-response curve. This, again, is a measure of the inclusion of $^3$H amino acids into the proteins of CHO cells. The results are expressed on the basis of percentage differences for the two extracts as measured against a control.

Further observations, during the experiments of the CHO cells, indicated the effects noted are not due to a toxic effect of the test materials on the cells. Thus, the viability of the cells is always good, as shown by the exclusion of the Trypan blue in a dye exclusion test. Likewise, it is noted that the cells stick to the plastic disk, i.e., cells living, and do not float to the top.

EXAMPLE 21

In order to further test the metabolic effects of the brain extract obtained as the second pool (G15 II) in Example 14, its effect of DNA synthesis of primary liver cells of rats is measured.

PREPARATION OF RAT LIVER CELLS

Collagenase Perfusion and Subcellular Fractionation of Rat Liver Cells

Perfusion was carried out on male Wistar rats (Mus Rattus Brunnthal, FRG, 150-200 g) as described in the literature by Williams. The wash-out perfusion medium, pH 7.4, contained NaCl (0.143 N), KCl (0.0067 N) and 2-hydroxyethylpiperaxine-N'-2ethanesulphonic acid (HERPES, 0.01 M). Perfusion with colleganase (Sigma type 1, 75 mg/150 ml activity in L-15 medium at pH 7.6) solution containing HEPES (0.05 M) was adjusted at a rate of 20 ml min$^{-1}$ and lasts for twenty minutes until serious leakages from the liver and points of cannulation and ligations occurred. Cells were detached into 50 ml of fresh collagenase solution at 37° C. for three minutes. The hepatocyte suspension was centrifuged at 150 rpm for five minutes. Liver cells were resuspended and washed in oxygenated L-15 medium 3×10 ml at 4° C. in order to remove collagenase. Viability as determined by trypan blue exclusion was in the range of 98 to 99% with a yield of 30 to 40% of the total weight of the liver. Preparations with lower viability were discarded.

The hepatocytes were diluted with L-15 medium pH 7.45, containing HEPES (0.02 M), to a final concentration of 2-4×10$^5$ hepatocytes ml$^{-1}$. Gentamicin sulphate (Sigma, Munich FRG, 50 µg ml$^{-1}$) was added to prevent bacterial growth. One ml aliquots of this suspension were transferred to plastic cell culture petri dishes, 3 cm in diameter.

In general, the test procedure with the rat cells was as follows:

1. As needed, new primary live cells of rats were prepared as described above.

2. Plastic plates containing 2-4×10$^5$ cells/ml were pre-incubated for 17-21 hours at 37° C. in an atmosphere containing pure 0$_2$. A change of medium was made after 4 hours.

3. After pre-incubation, sample of various concentration of test materials were added to the plates. For control purposes, plates containing only L-15 medium were used. These plates were then incubated for the desired period of time.

4. After the incubation period, cells were washed 5 times with 2 mM cold Thymide and then the cells were killed with 7% trichloracetic acid solution.

5. The dead cells were scraped from the bottom of the plates and filtered through a GFC filter. The Thymide incorporation was measured by liquid scintillation counting.

6. The incorporated thymidine was measured in decompositions per minute and expressed as percent of control.

7. Each test was done with three or more plates of material and then each test was repeated at least three times.

Figure 5:
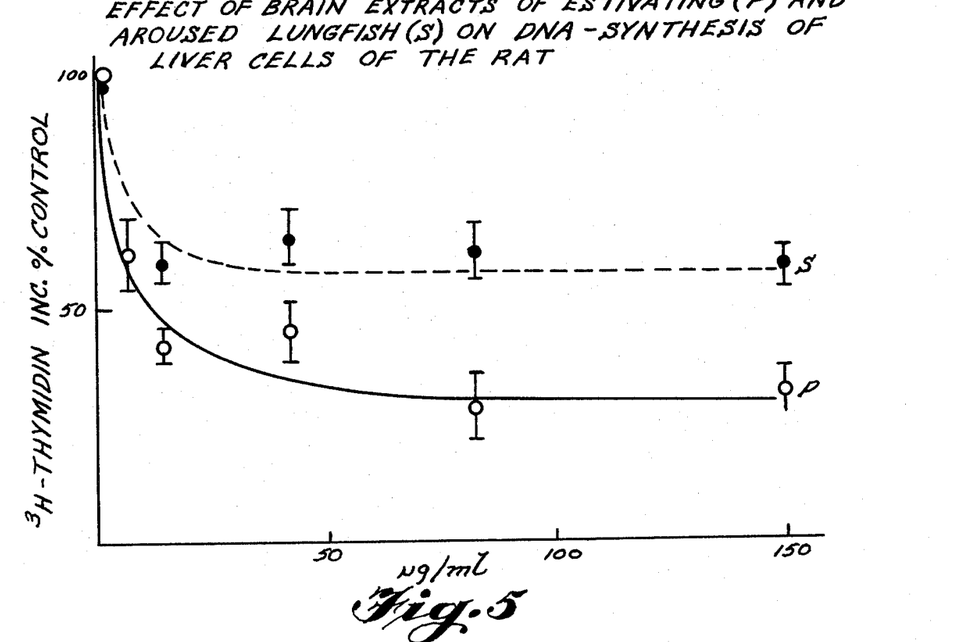
FIG. 5 shows the effect of brain extracts (material of G15 II) of estivating and aroused lungfish on DNA-synthesis of liver cell of the rat.

The results of this testing is shown in FIG. 5, wherein, a dose-response curve for the extracts of estivating and aroused lungfish has been plotted. The test conditions were labeled time=20 minutes; incubation time=40 minutes.

It is to be noted that this dose-response curve shows there is a maximum of about a 70% decrease in DNA synthesis of estivating lungfish which is approached asymptotically at a concentration of G15 II of 100 $\mu$g/ml. The G15 II pool of aroused lungfish, i.e., material refined in the same manner as that from an estivating lungfish, had a maximum of a 40% decrease on DNA synthesis which is approached asymtotically at a concentration of 20 mg/ml. The significance of the difference is assured by Student's t-test at a level of P 0.05 at a concentration of from 50 to 150 $\mu$g/ml.

Pronase P degradation is measured under conditions listed in Table 6. This data show the effect on DNA and protein synthesis of CHO cells is destroyed completely, whereas, on rat liver cells DNA synthesis is partly destroyed as shown in Table 6.

TABLE 6

INCUBATION OF IN VITRO DNA-SYNTHESIS REDUCING BRAIN EXTRACTS FROM ESTIVATING LUNGFISH WITH PRONASE

| | 6-$^3$H thymidine inc. into DNA* (% of control) | | |
|---|---|---|---|
| | Rat Liver Cells | | CHO Cells |
| | a | b | c |
| active extract | 33.9 ± 10.5 | 53.1 ± 5.0 | 71.4 ± 6.8 |
| active extract after pronase inc. | 66.6 ± 5.1 | 80.5 ± 8.2 | 95.8 ± 5.6 |
| Pronase alone | | 103.5 ± 10.5 | 105.0 ± 10.1 |

| | $^3$H aminoacids inc. into proteins* (% of control) CHO Cells |
|---|---|
| | c |
| active extract | 80.7 ± 1.7 |
| active extract after pronase inc. | 93.0 ± 6.2 |

*$\mu$g extract incubated: a = 220, b = 100, c = 280

EXAMPLE 22

9 mg of freeze dried material of the second pool of material (G15 II) from Example 14, is dissolved in 500 $\mu$l of 0.04% trifluoroacetic acid and this solution is then fed to a gel chromatography column containing BIO-GEL P2-400 molecular sieve. The BIOGEL sieve has a fractionation range of from about 1800 to about 300. The column's dimensions are 1 cm diameter and 136 cam length. The flow rate of effluent is 2 ml per 40 minutes. The eluant used is 0.04% trifluoroacetic acid.

Figure 6:
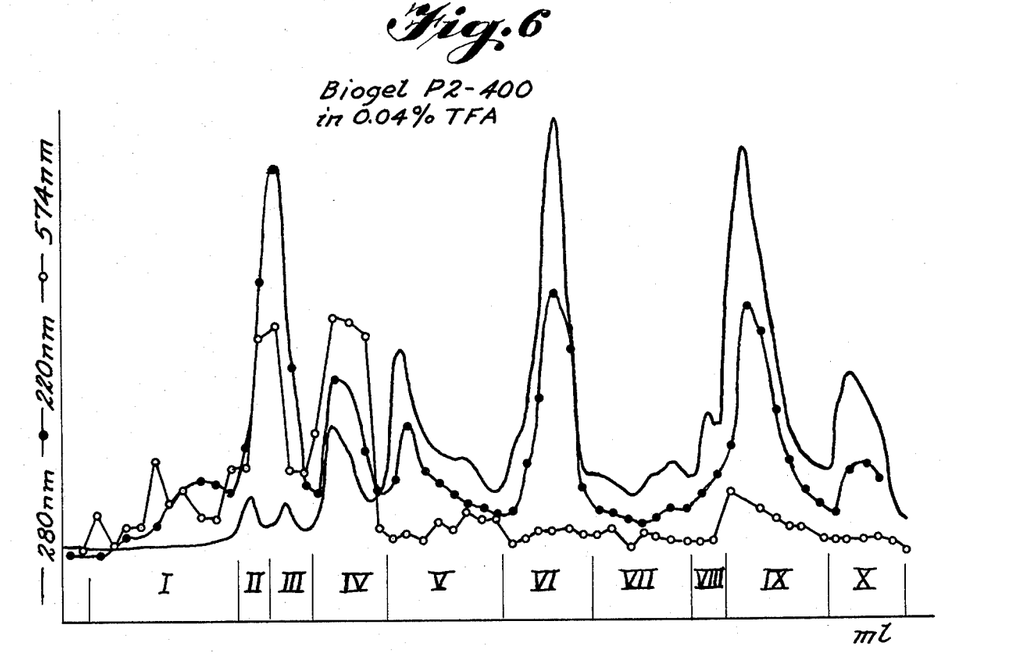
FIG. 6 shows the UV absorbance vs. fraction number for fractions obtained in Example 22.

The UV absorption of the fractions at 220 nm, 254 nm and 280 nm, as well as 570 nm, after ninhydrin reaction, are monitored and is recorded in FIG. 6. The peaks are tested for effects on DNA synthesis of CHO cells. Activity is found in fractions constituting peaks 2 & 3, and to a lesser amount in fractions constituting peak 1. About 60% of the expected activity is found in the second and third pools.

EXAMPLE 23

5 mg of freeze dried material obtained in the third pool of material from the BIOGEL separation, is dissolved in 2% acetic acid and this solution is then fed to a chromatography column containing DOWEX 50-W-X-4 cationic ion exchange resin. The column dimensions are 1 cm diameter and 28 cm length. The resin in the column prior to use is equilibrated with an 0.2 molar solution of Pyridine Acetate at pH 3.24 at 51° C. The eluant is 100 ml of the above Pyridine acetate solution at the same pH. One fraction of 8 ml is obtained over a period of 15 minutes. Thereafter, a linear pH gradient is used with reservoir being dual 300 ml vessels. One vessel contains 300 ml 3 M Pyridine Acetate at pH 5.15 and the other 300 ml 0.2 M Pyridine Acetate at pH 3.24. The UV absorption of the fractions at 570 nm after ninhydrin reaction is monitored and is recorded in FIG. 7. Cuts of material are made under the 12 peaks and each of these is tested for effects on DNA synthesis of CHO cells. Activity is found in the peak corresponding to peak E.

EXAMPLE 24

The product obtained in Example 23 is further refined by subjecting the product to a first high pressure liquid chromatography step. The chromatography apparatus used is manufactured by Hewlett-Packard, Inc. A 5$\mu$ Merck RP 18 Hibar Reversed Phase column, 240 mm long and 4.6 mm in diameter is used.

Figure 8:
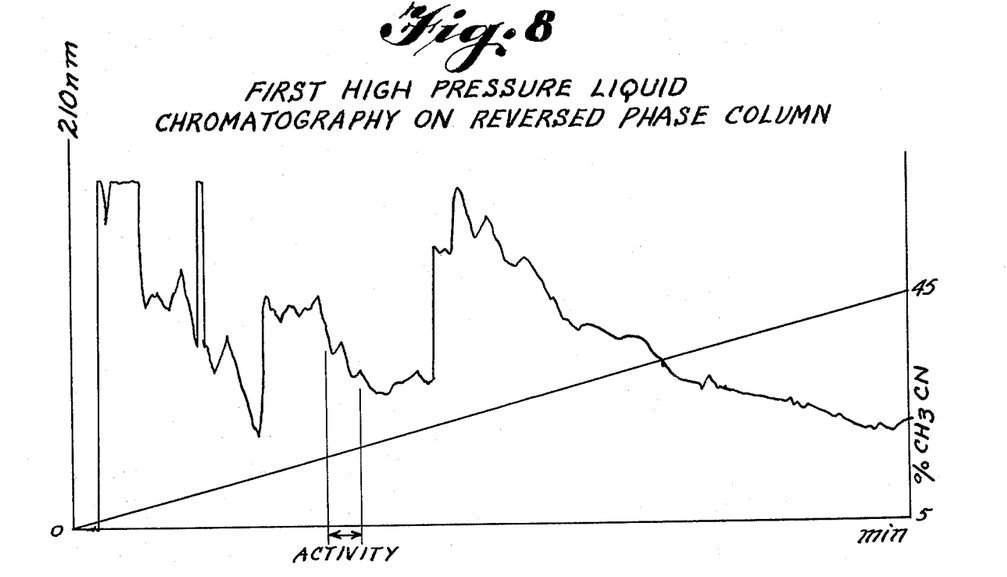
FIG. 8 shows the UV absorbance vs. time for fractions obtained in Example 24.

The product is dissolved in 0.005 mM Na$_2$HPO$_4$ solution and adjusted to a pH of 3.1 with phosphoric acid. Acetonitrile (Uvasol-Merck) is used as the eluant. The solution is eluted a gradient of 5% to 45% in 30 minutes. The UV absorbance of the solution is monitored at 210 nm. The results are shown in FIG. 8.

Active fractions are those collected between the 9th and 11th minutes, inclusive. The concentration of acetonitrile in the fractions is from 17 to about 20%.

EXAMPLE 25

The active fractions from Example 26 are subjected to a second high pressure liquid chromatography using a column having the same packing and dimensions as that used in Example 24. The active fractions are dissolved in 0.005 M KH$_2$PO$_4$ solution and adjusted to a pH of 3.1 with phosphoric acid. The eluant is acetonitrile (Uvasol-Merck). The solution is eluted at a gradient of 5 to 25% in 30 minutes. UV absorbance of the solution at 210 nm is monitored. The results are shown in FIG. 9.

Figure 9:
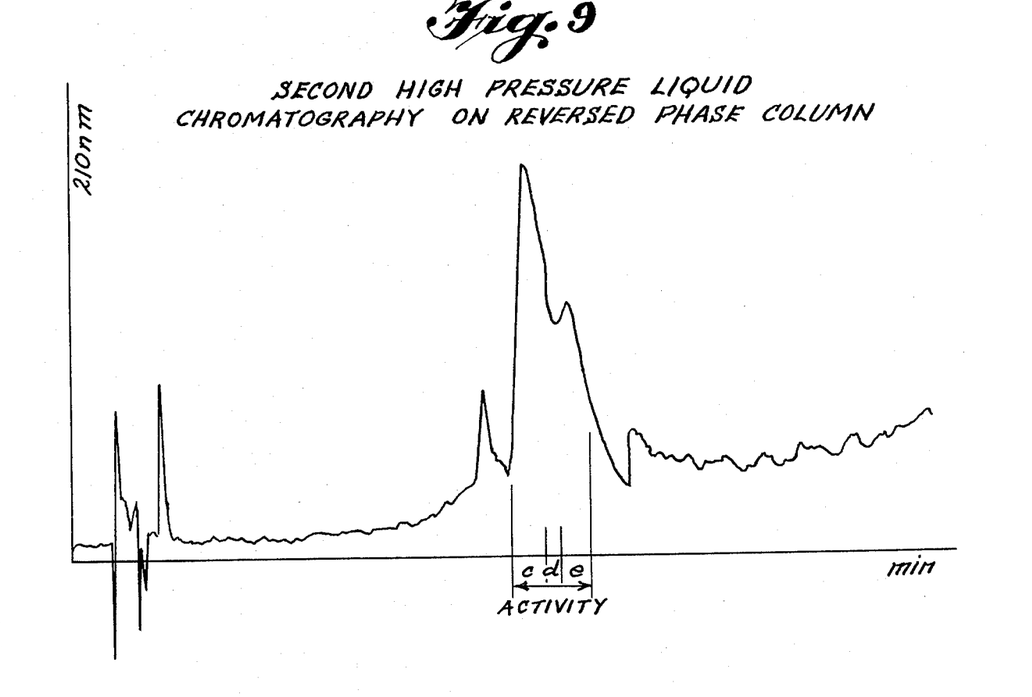
FIG. 9 shows the UV absorbance vs. time for fractions obtained in Example 25.

Fractions representing peaks c, d and e in FIG. 9 have been found to show antimetabolic activity. The so-obtained product is a hormone-like peptide having high purity.

EXAMPLE 26

The peptide obtained in Example 25 representing peaks c and e in FIG. 9 are tested for their antimetabolic activity. The experimental procedure outlined in Example 19 is repeated with a protion of the above-mentioned peptide to determine the effect of the peptide on DNA-synthesis of Chinese Hamster Ovary cells (CHO).

The results show that the dose is 40 picomole of the peptide per plate for a 25% reduction of DNA synthesis.

EXAMPLE 27

The peptides of Example 25, representing peaks c and e in FIG. 9, are used for amino acid analysis by means of a Durram column. Both analyses show an amino acid composition of:

| 0–1 | asp |
| 3 | ser |
| 2 | gln |
| 1 | pro |
| 1–2 | gly |
| 1 | val |
| 1–2 | lys |
| 1 | arg |

EXAMPLE 28

The amino acid sequence of each of the peptide portions representing peaks c, d and e in FIG. 9 is determined by using a sequencer constructed by P. Edman of the Max Planck Institute for Biochemistry, Munich, West Germany. The program used for such determination is the standard program used for small peptides. 1 mg of polybren is added to each of the portions.

Identical amino acid sequences are obtained for the three portions. The results show that the portions contain peptides of at least about 95% purity. The following sequence is obtained:

ser-arg-val-lys-gln-val-gly-ser-ser-pro-gln

The molecular weight of the peptide is about 1352.5.

EXAMPLE 29

A pool of the brain extract material representing fraction I in FIG. 6 is subjected to further testing as follows, the fraction possessing activity.

Figure 7:
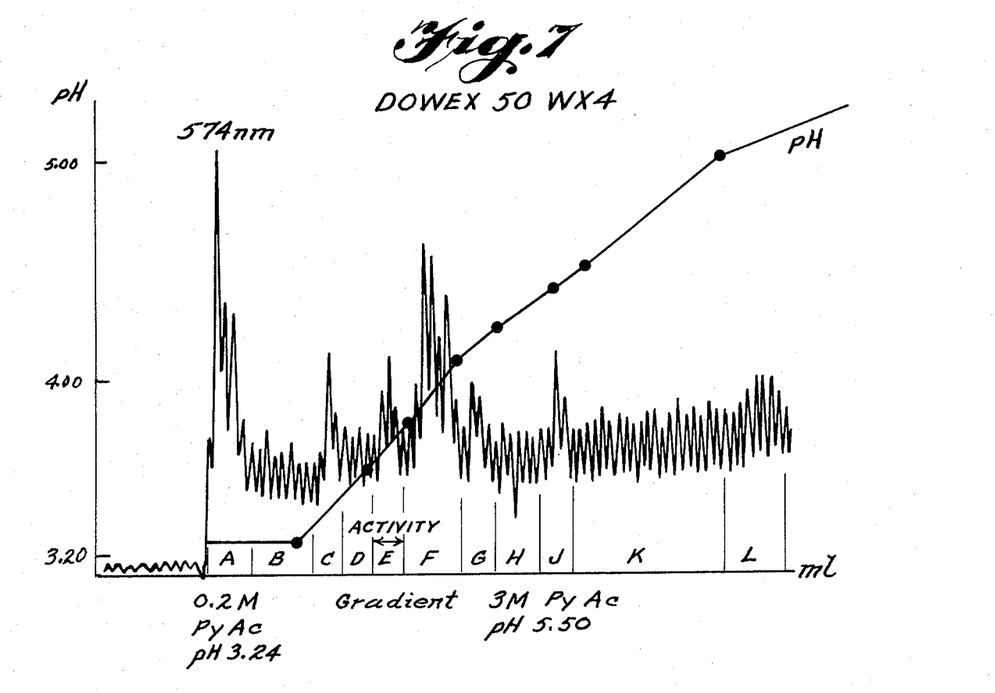
FIG. 7 shows the UV absorbance after ninhydrin reaction vs. fraction number for fractions obtained in Example 23.
Figure 10:
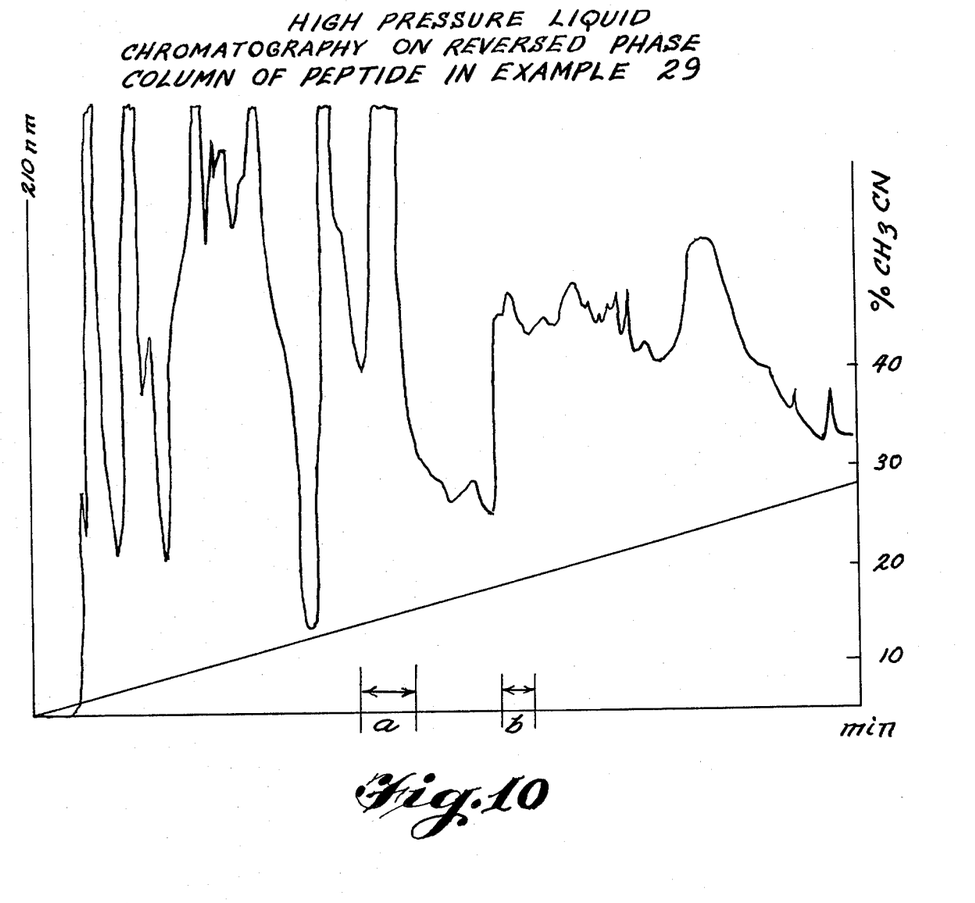
FIG. 10 shows the UV absorbance vs. time for fractions obtained in Example 29.

Aliquots of the above-mentioned brain extract is fed to a chromatography column containing DOWEX 50-W-X-4 cationic ion exchange resin. The procedure and apparatus used here are the same as that used in Example 23. The UV absorbance of the fractions at 570 nm is monitored. A response curve similar to that shown in FIG. 7 is obtained. Fractions which possess biological activity, e.g. lowering of DNA-synthesis of test animals, are collected and subjected to one high pressure liquid chromatography step using the procedure and apparatus outlined in Example 27. The results are shown in FIG. 10.

All fractions so obtained are tested for their biological activity e.g. effect on DNA synthesis of CHO cells, using the procedure and apparatus described in Example 19. Fractions 15 to 16 and 21, shown as fractions a and b in FIG. 10, have been found to increase the DNA synthesis of CHO cells by about 30%.

What I claim is:

1. A hormone-like peptide having antimetabolic activity comprising a peptide of the formula:

a-$X_1$-arg-val-$X_2$-gln-val-gly-$X_3$-$X_4$-pro-$X_5$-(gly)$_n$-(asp)$_m$-c, and wherein, a is a member of the group consisting of a free amino group, and an acylated amino group;

$X_1$ is a member of the group consisting of ser, gln, glu, and pyr-glu;

$X_2$ is a member of the group consisting of lys and ser;

$X_3$ is a member of the group consisting of ser and asn;

$X_4$ is a member of the group consisting of ser, gln, and lys;

$X_5$ is a member of the group consisting of gln and ser;

c is a member of the group consisting of a free acid group and an acid amide group;

n=0 or 1 and, m=0 or 1, provided that when n=0, m=0.

2. The peptide of claim 1, wherein $X_1$ is ser, $X_2$ is lys, $X_3$ is ser, $X_4$ is ser, and $X_5$ is gln.

3. The peptide of claim 2, wherein n=1 and M=0.

4. The peptide of claim 2, wherein n=m=1.

5. The peptide of any one of claims 1, 2, 3 or 4, wherein the acid groups of the side chains in said peptide is selected from the group consisting of free acids and acid amide.

6. The peptide of any one of claims 1, 2, 3 or 4, wherein the amino groups of the side chains in said peptide are selected from the group consisting of free amino groups and acylated amino groups.

7. A process of decreasing oxygen consumption in animals comprising administering a pharmacologically effective amount of the peptide of claim 1 to said animal.

8. A process of effecting hypothermia in animals comprising administering a pharmacologically effective amount of the peptide of claim 1 to said animal.

* * * * *